United States Patent [19]

Foguet Ambros et al.

[11] Patent Number: 5,852,021
[45] Date of Patent: Dec. 22, 1998

[54] POLYMORPH B OF 1-(DIPHENYLMETHYL)-4-[3-(2-PHENYL-1,3-DIOXOLAN-2-YL) PROPYL] PIPERAZINE

[75] Inventors: Rafael Foguet Ambros; Lluis Anglada Burniol; Manuel Raga Carreño; Jose A. Ortiz Hernandez; Aurelio Sacristan Munoz; Josep M. Castello Barenys, all of Barcelona, Spain

[73] Assignee: Ferrer Internacional, S.A., Barcelona, Spain

[21] Appl. No.: 750,131

[22] PCT Filed: Mar. 28, 1995

[86] PCT No.: PCT/ES95/00033

§ 371 Date: Dec. 27, 1996

§ 102(e) Date: Dec. 27, 1996

[87] PCT Pub. No.: WO96/30366

PCT Pub. Date: Oct. 3, 1996

[51] Int. Cl.$^6$ ............... A61K 31/495; C07D 405/06
[52] U.S. Cl. ............................... 514/255; 544/374
[58] Field of Search ............... 514/255; 544/374

[56] References Cited

U.S. PATENT DOCUMENTS 4,883,797  11/1989  Foguet et al. ............ 514/255

FOREIGN PATENT DOCUMENTS 0097340  1/1984  European Pat. Off. .

OTHER PUBLICATIONS

S. Gubert et al., Arneimittel Forschung Drug Research, vol. 37, No. 10, (1987), *Synthesis of Some N–Benzhydrylpiperazine Derivatives as Calcium Antagonists*, pp. 1103–1107.

*Primary Examiner*—Mukund J. Shah
*Assistant Examiner*—Brenda Coleman
*Attorney, Agent, or Firm*—Birch, Stewart, Kolasch & Birch

[57] ABSTRACT

Polymorph B of (1-diphenylmethyl)-4-[3-(2-phenyl-1,3-dioxolan-2-yl)propyl]piperazine have been identified. A process for its preparation and its use are described.

4 Claims, 8 Drawing Sheets

Fig. 4: X-ray diffractogram of Dotarizine polymorph A.

IR spectrum of Dotarizine polymorph B (2000–400 cm$^{-1}$).

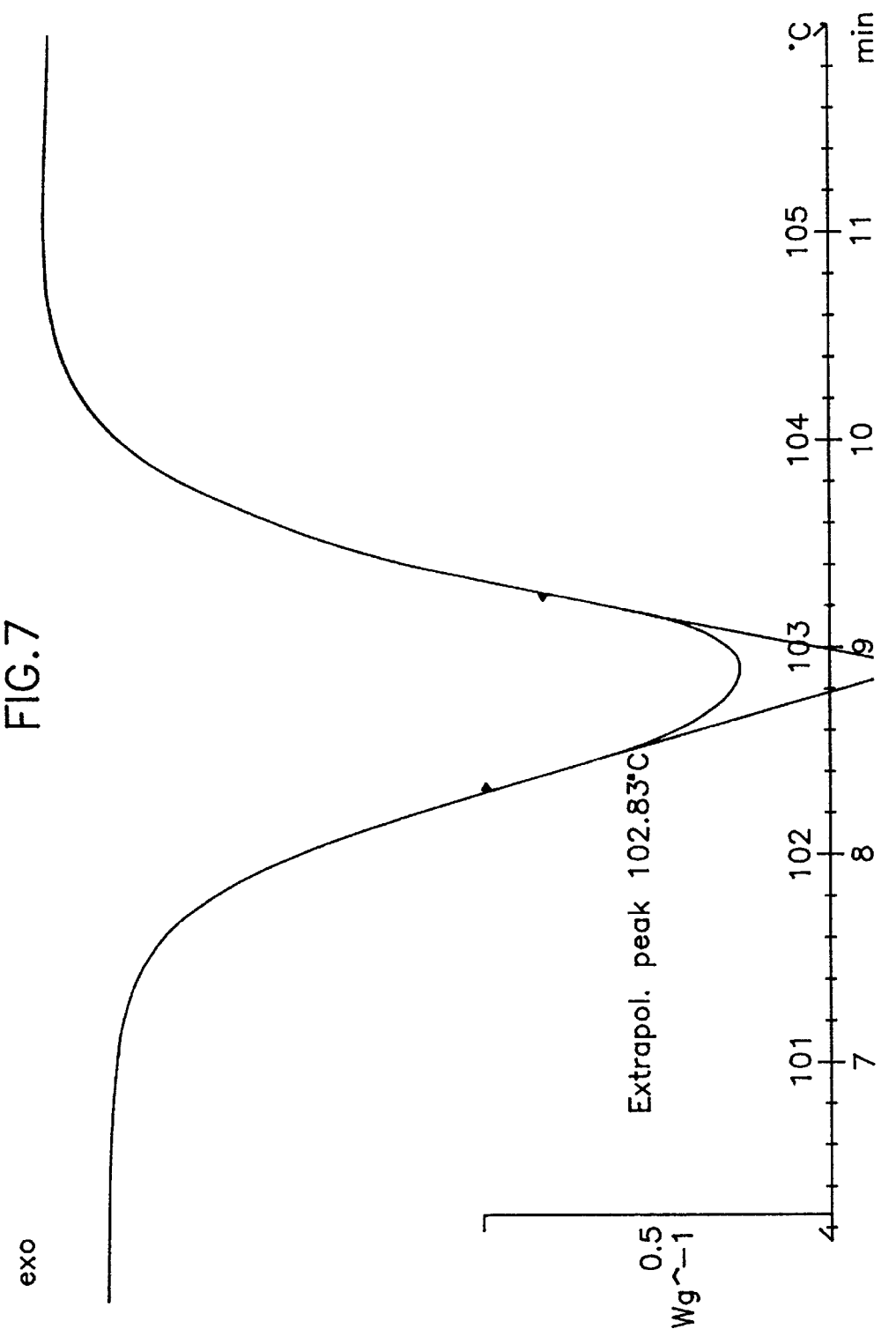
FIG.7 Differential Scanning Calorimetry (DSC) Thermogram of Dotarizine polymorph B.

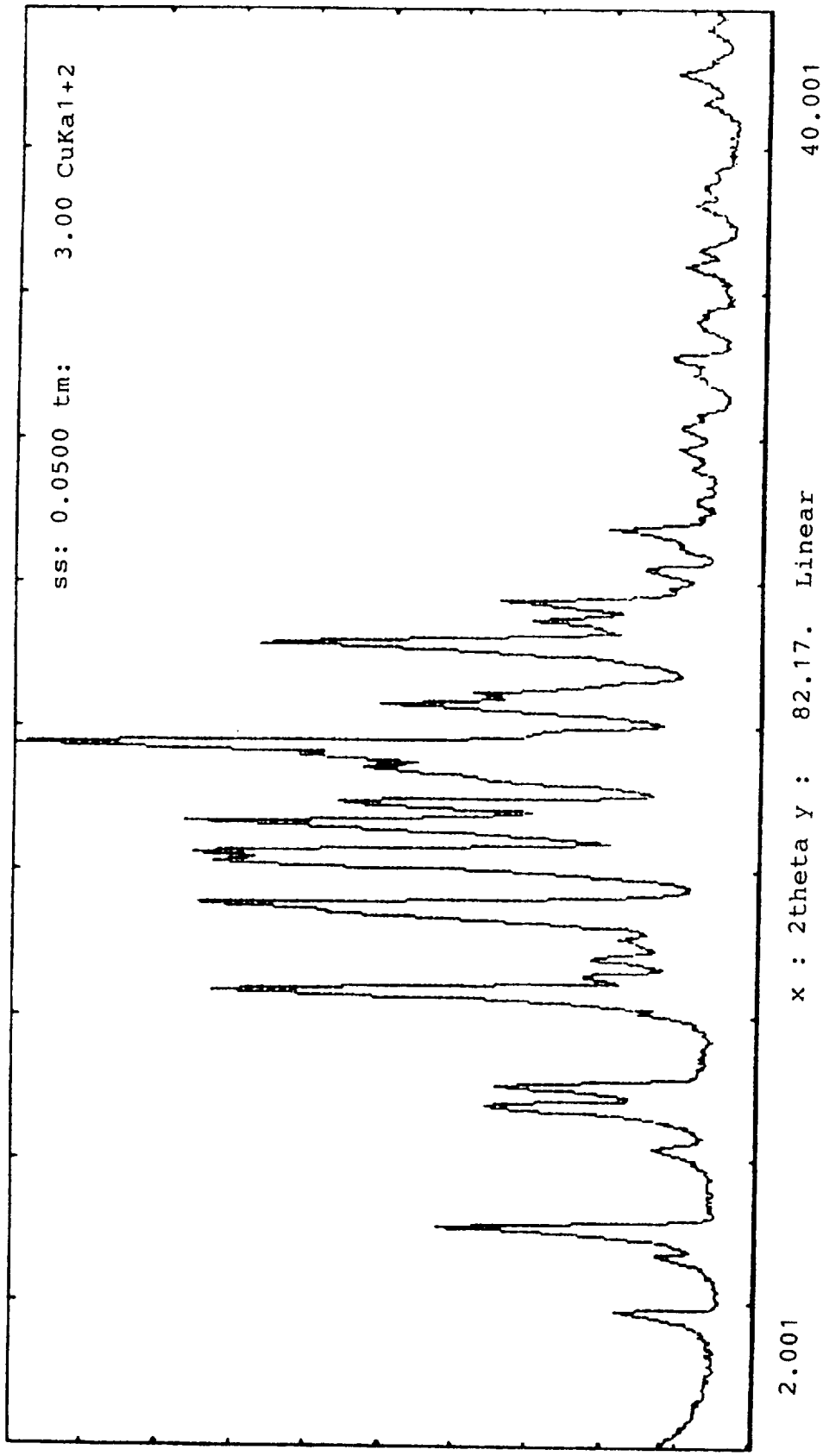
Fig. 8: X-ray diffractogram of Dotarizine polymorph B.

5,852,021

POLYMORPH B OF 1-(DIPHENYLMETHYL)-4-[3-(2-PHENYL-1,3-DIOXOLAN-2-YL) PROPYL] PIPERAZINE

The present application is a § 371 of PCT/ES95/00033 filed on Mar. 28, 1995.

The present invention relates to novel Polymorph B of 1-(Diphenylmethyl)-4-[3-(2-phenyl-1,3-dioxolan-2-yl) propyl]piperazine-compound known as dotarizine (WHO).

BRIEF DESCRIPTION OF THE DRAWINGS

FIG. 7 is a differential scanning calorimetry (DSC) thermogram of dotarizine Polymorph B.

FIG. 8 is an X-ray powder diffractogram of dotarizine Polymorph B.

Figure 1:
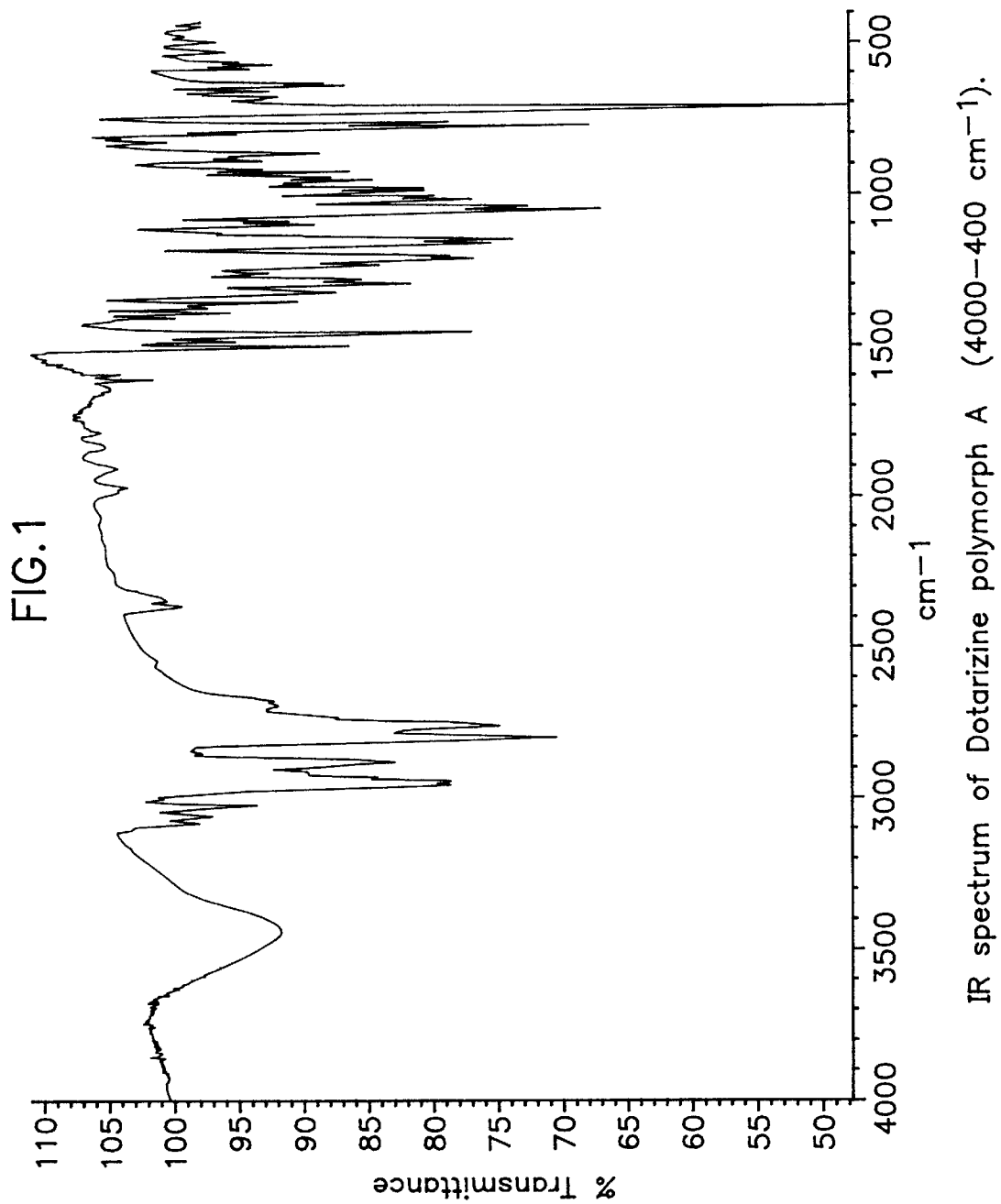
FIG. 1 is an infrared (IR) spectrum of dotarizine Polymorph A at the range from 4000 to 400 $cm^{-1}$.
Figure 2:
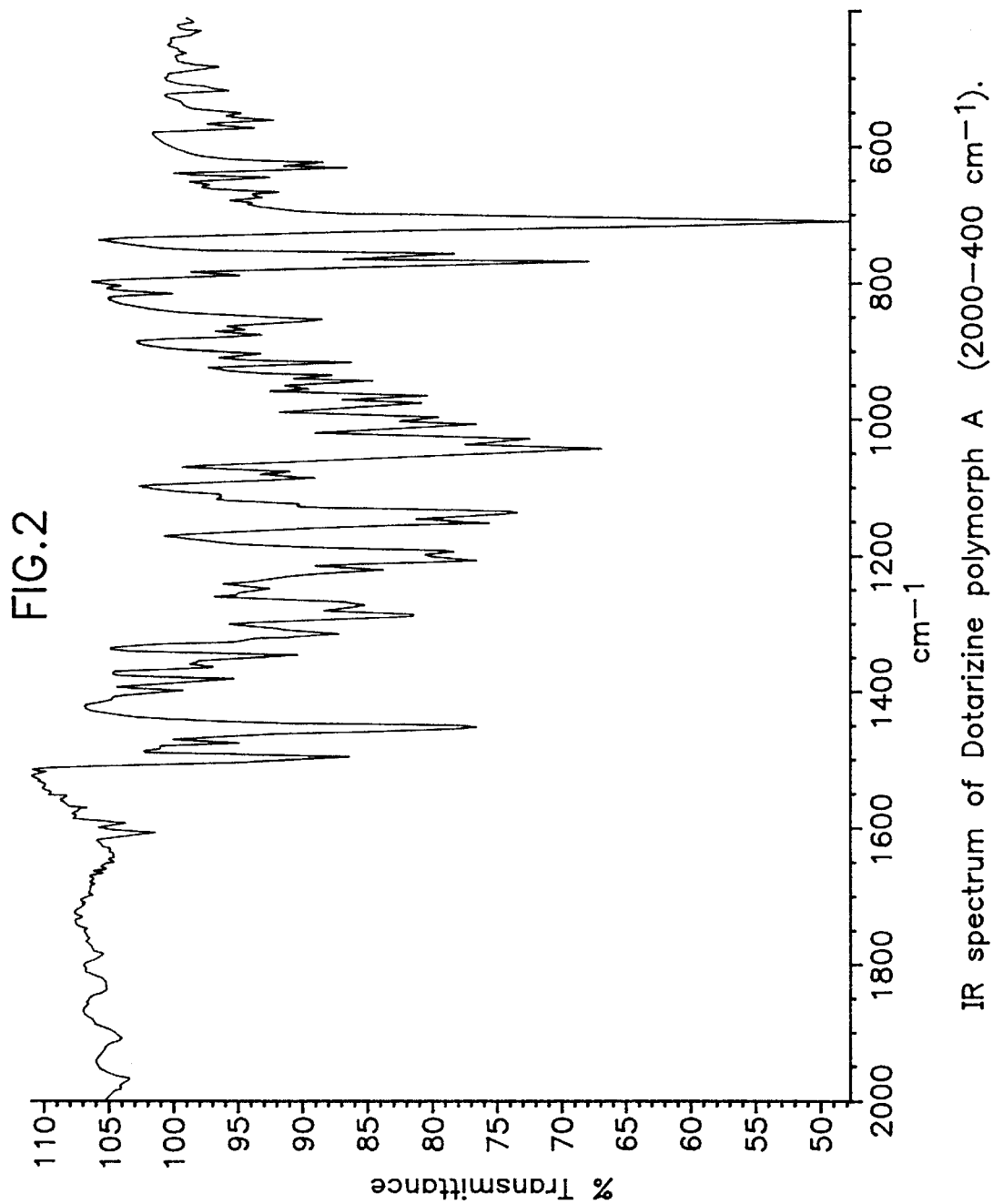
FIG. 2 is an infrared (IR) spectrum of dotarizine Polymorph A at the range from 2000 to 400 $cm^{-1}$.
Figure 3:
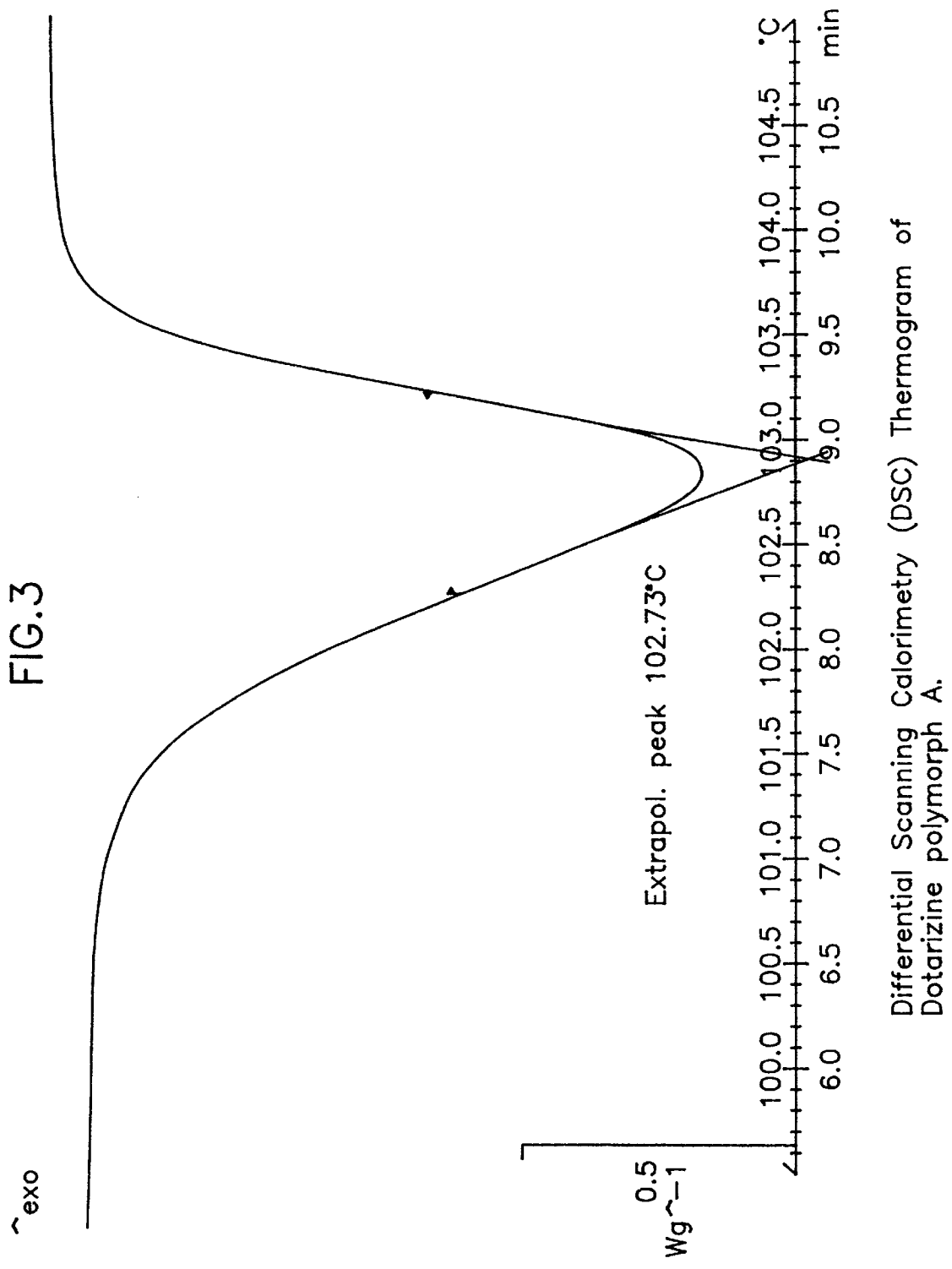
FIG. 3 is a differential scanning calorimetry (DSC) thermogram of dotarizine Polymorph A.
Figure 5:
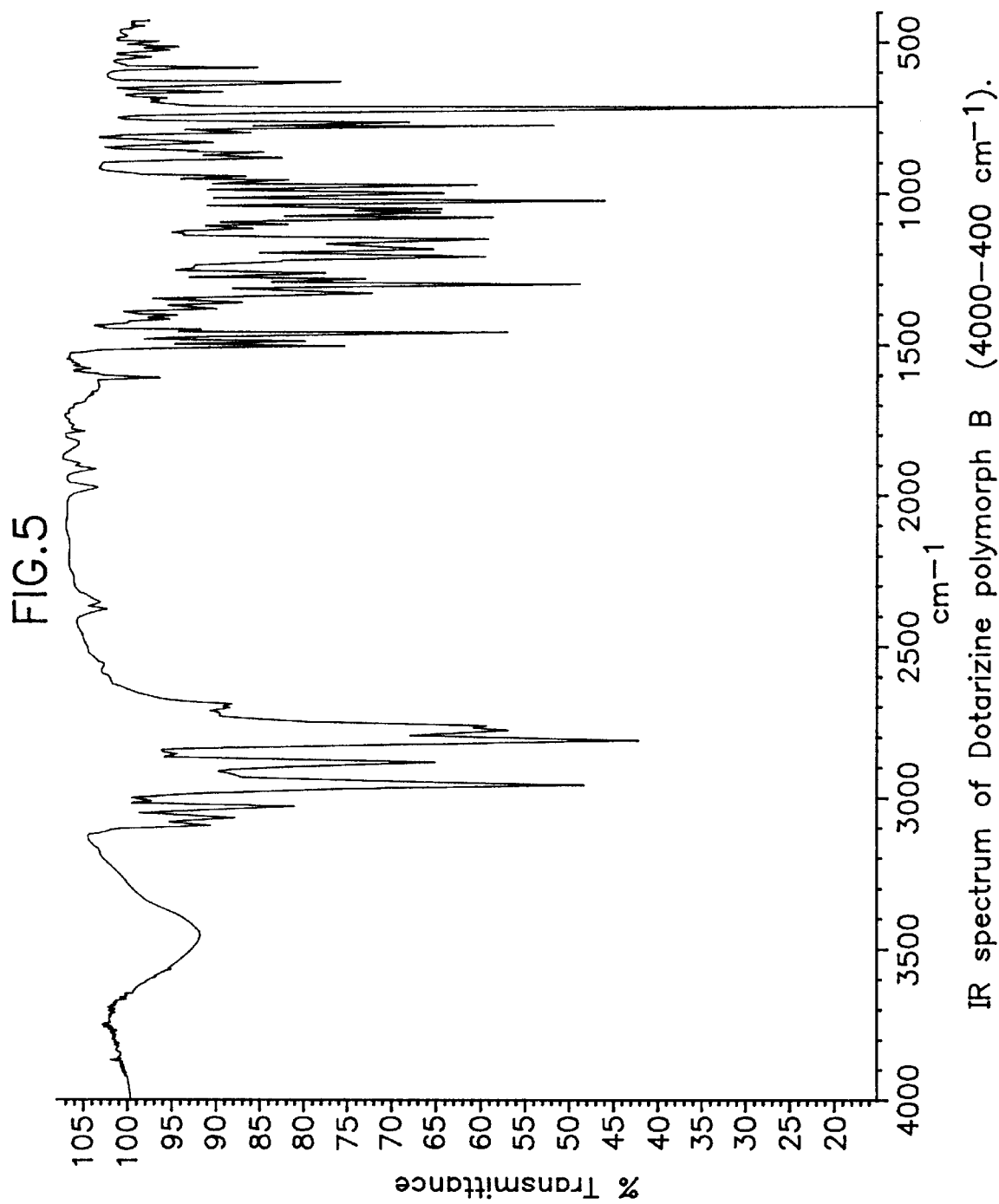
FIG. 5 is an infrared (IR) spectrum of dotarizine Polymorph B at the range from 4000 to 400 $cm^{-1}$.

DETAILED DESCRIPTION OF THE INVENTION 1-(Diphenylmethyl)-4-[3-(2-phenyl-1,3-dioxolan-2-yl) propyl]piperazine is an antiserotonergic agent ($5HT_{1c}$ and $5HT_2$) and calcium antagonist. This compound is effective in the prophylaxis of migraine and in the treatment of vertigo. The preparation of this compound was disclosed in European Patent No. 0097340 showing a melting point of 93°–97° C. The applicants have found out that dotarizine exhibits two novel polymorphs, A and B, which have a melting point in the range between 100° and 103° C. The differential scanning calorimetry (DSC) thermograms of both polymorphs do not show significant differences as illustrated in FIGS. 3 and 7. Nevertheless, the applicants have found out that their IR spectra do show significant differences especially in the range 1100–900 $cm^{-1}$ in accordance with the enlarged IR spectra in FIGS. 2 and 6. Dotarizine polymorph A is characterized by showing bands at 2962, 2949, 2808, 2767, 1446, 1040, 1025, 1002, 993, 970, 960, 761 and 707 $cm^{-1}$ and dotarizine polymorph B is characterized by showing bands at 2961, 2883, 2812, 2777, 2760, 1448, 1283, 1058, 1042, 1029, 1006, 978, 951, 758 and 703 $cm^{-1}$ (FIGS. 1 and 5). The present invention provides a process for obtaining selectively both polymorphs of dotarizine; polymorph A is obtained by crystallization in methanol, while polymorph B is obtained by crystallization in n-hexane.

The use of polymorph A for preparing pharmaceutical formulations in the form of drops (suspensions) is recommended, while the use of polymorph B for preparing capsules or other solid forms is preferred.

Polymorphs A and B of dotarizine mixed with pharmaceutically acceptable carriers can be administered at daily doses ranging from 50 and 150 mg.

The following examples will illustrate the preparation of polymorphs A and B of dotarizine and pharmaceutical formulations containing them. The examples are not intended to limitate the scope of the invention as defined hereinabove or as claimed hereinafter.

EXAMPLE 1

Polymorph A of 1-(diphenylmethyl)-4-[3-(2-phenyl-1,3-dioxolan-2-yl) propyl) piperazine 11.2 g of dotarizine are dissolved in 56 ml of methanol at reflux. The solution is filtered and allowed to crystallize at a temperature of between 20° and 25° C. with gentle stirring. A crystalline solid is formed, which weighs 9.9 g (yield 88.5%) after dried.

IR spectrum (KBr), range from 4000 to 400 $cm^{-1}$: FIG. 1.

IR spectrum (KBr), range from 2000 to 400 $cm^{-1}$: FIG. 2.

Differential scanning calorimetry (DSC) thermogram: FIG. 3.

Figure 4:
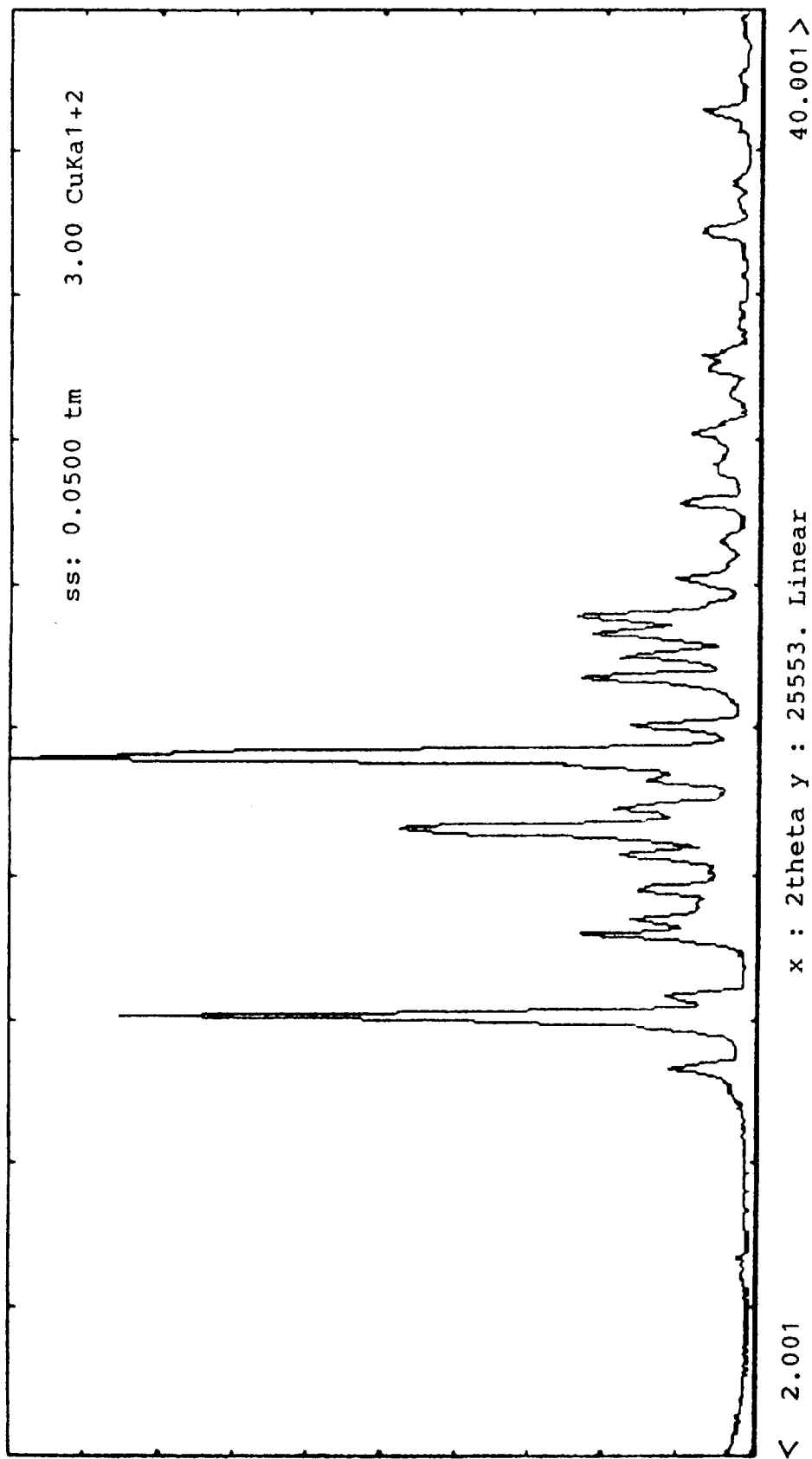
FIG. 4 is an X-ray powder diffractogram of dotarizine Polymorph A.

X-ray powder diffractogram: FIG. 4.

EXAMPLE 2

Polymorph B of 1-(diphenylmethyl)-4-[3-(2-phenyl-1,3-dioxolan-2-yl) propyl)piperazine 10 g of dotarizine are dissolved in 100 ml of n-hexane at reflux. The solution is filtered and allowed to crystallize at a temperature of between 20° and 25° C. with stirring. A crystalline solid is formed, which weighs 7.6 g (yield 76%) after dried.

IR spectrum (KBr), range from 4000 to 400 $cm^{-1}$: FIG. 5.

Figure 6:
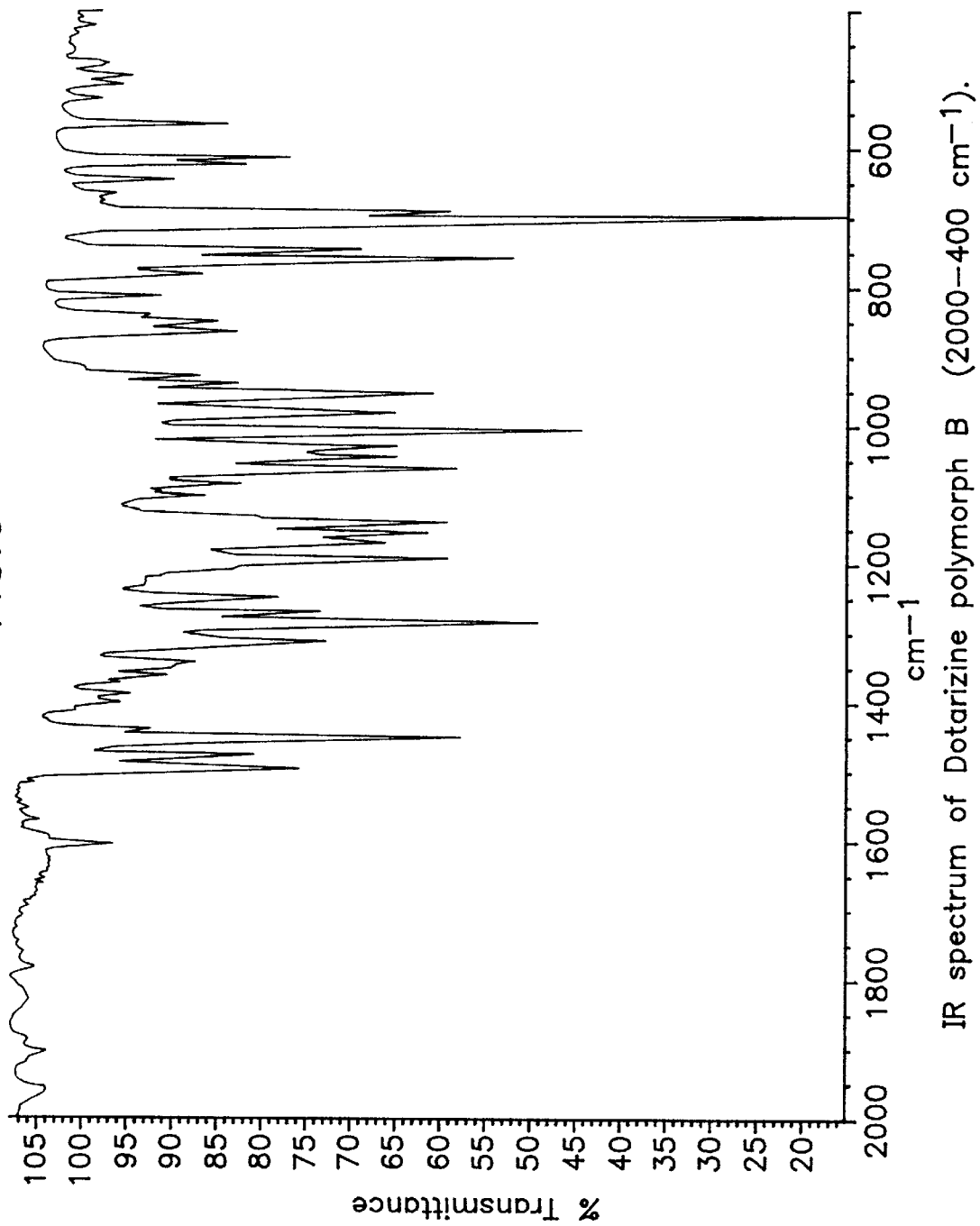
FIG. 6 is an infrared (IR) spectrum of dotarizine Polymorph B at the range from 2000 to 400 $cm^{-1}$.

IR spectrum (KBr), range from 2000 to 400 $cm^{-1}$: FIG. 6.

Differential scanning calorimetry (DSC) thermogram: FIG. 7.

X-ray powder diffractogram: FIG. 8.

EXAMPLE 3

Drops

Composition for 100 ml:
Dotarizine polymorph A. . . 7.50 g
Sucrose. . . 30.00 g
Microcrystalline cellulose RC-581. . . 1.00 g
Carboxymethylcellulose sodium. . . 0.10 g
Saccharin sodium. . . 3.50 g
Methyl-p-hydroxybenzoate. . . 0.15 g
Propyl-p-hydroxybenzoate. . . 0.03 g
Polysorbate 80. . . 0.20 g
Distilled water q.s. . . . 100.00 ml

EXAMPLE 3

Capsules

Composition for 1 capsule
Dotarizine polymorph B. . . 50.0 mg
Silicon dioxide. . . 2.0 mg
Croscarmellose sodium. . . 8.0 mg
Corn starch. . . 50.0 mg
Talc. . . 8.0 mg
Magnesium stearate. . . 1.5 mg
Microcrystalline cellulose q.s. . . . 210.0 mg

We claim:

1. Polymorph B of 1-(diphenylmethyl)-4-[3-(2-phenyl-1,3-dioxolan-2-yl)propyl]piperazine exhibiting IR bands at 2961, 2883, 2812, 2777, 2760, 1448, 1283, 1058, 1042, 1029, 1006, 978, 951, 758 and 703 $cm^{-1}$ as presented in FIGS. 5 and 6.

2. A process for the preparation of Polymorph B of 1-(diphenylmethyl)-4-[3-(2-phenyl-1,3-dioxolan-2-yl)

propyl]piperazine which comprises dissolving 1-(diphenylmethyl)-4-[3-(2-phenyl-1,3-dioxolan-2-yl) propyl]piperazine in n-hexane; and allowing crystalline Polymorph B to form.

3. A pharmaceutical composition containing the polymorph and pharmaceutically acceptable carriers according to claims 1 or 2, which is useful in the prophylaxis of migraine and in the treatment of vertigo.

4. A method for the prophylaxis of migraine and the treatment of vertigo which comprises treating patients in need thereof with an effective amount of the compound according to claim 1.

\* \* \* \* \*